United States Patent [19]

Favin et al.

[11] Patent Number: 5,371,597
[45] Date of Patent: Dec. 6, 1994

[54] SYSTEM AND METHOD FOR MEASURING POLARIZATION DEPENDENT LOSS

[75] Inventors: David L. Favin, Little Silver; Bruce M. Nyman, Freehold Township, Monmouth County; Gregory M. Wolter, Oakhurst, all of N.J.

[73] Assignee: AT&T Corp., Murray Hill, N.J.

[21] Appl. No.: 156,602

[22] Filed: Nov. 23, 1993

[51] Int. Cl.⁵ .............................. G01J 4/00
[52] U.S. Cl. ............................. 356/367; 356/364
[58] Field of Search .......... 356/369, 365, 366, 367, 356/368; 250/225

[56] References Cited

U.S. PATENT DOCUMENTS

| | | | |
|---|---|---|---|
| 4,306,809 | 12/1981 | Azzam | 356/368 |
| 5,227,623 | 7/1993 | Heffner | 356/364 |
| 5,247,176 | 9/1993 | Goldstein | 356/368 |
| 5,298,972 | 3/1994 | Heffner | 356/364 |

*Primary Examiner*—Richard A. Rosenberger

[57] ABSTRACT

Polarization dependent loss (PDL) of an optical component is computed in a deterministic method that requires only four measurements, each having a unique input state of polarization.

15 Claims, 1 Drawing Sheet

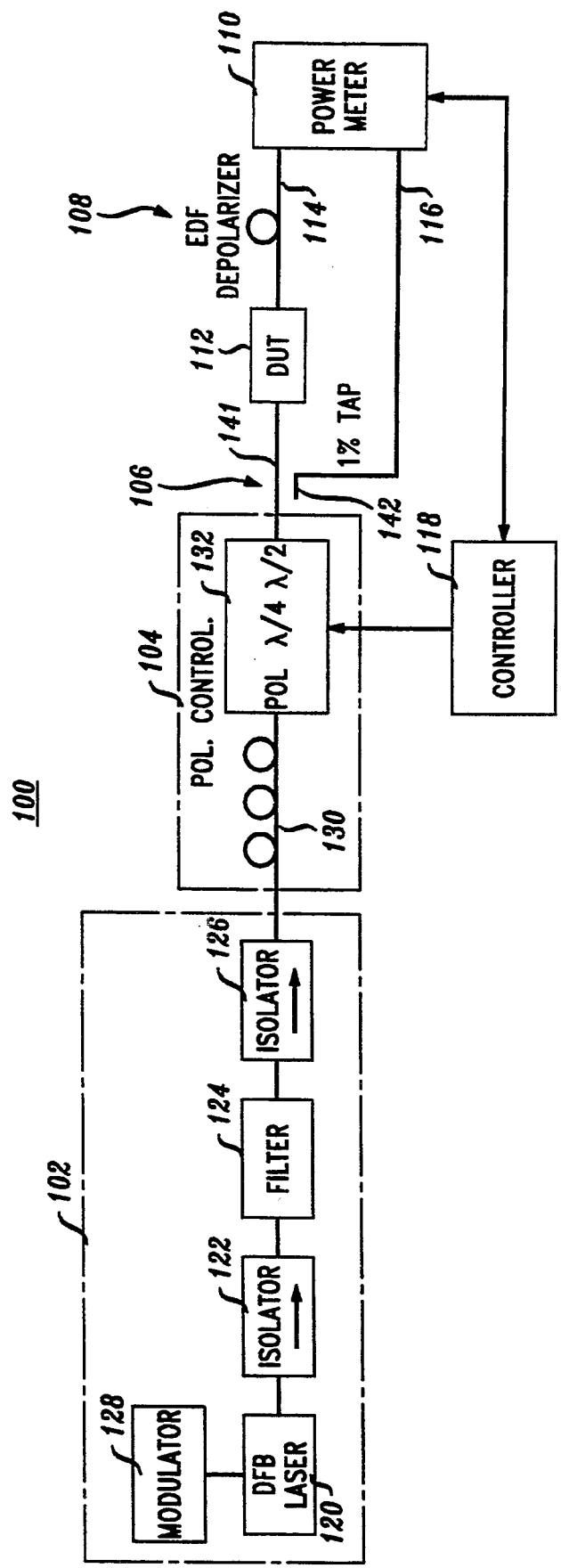

SYSTEM AND METHOD FOR MEASURING POLARIZATION DEPENDENT LOSS

BACKGROUND OF THE INVENTION

1. Field of the Invention

The present invention relates to the field of optics, and more particularly, to a method and apparatus for measuring the polarization dependent loss of an optical component.

2. Related Art

When an optical signal is input to an optical component, an insertion loss occurs. A portion of the insertion loss varies as a function of the input polarization state and is known as polarization dependent loss (PDL). PDL causes signal degradation in optical transmission systems. Many optical components, such as isolators and couplers, exhibit PDL. It is desirable to accurately measure the PDL of an optical component to determine its suitability for use in an optical system.

Conventional techniques have allowed measurement of PDL to an accuracy of approximately 0.01 dB. However, in an optical transmission system which spans thousands of kilometers and includes many optical components located along the transmission path, a PDL of 0.01 dB per component can have a substantial adverse affect on signal quality. Thus, it is desirable to increase the accuracy with which PDL can be measured so that optical components may be more accurately screened to determine suitability for use in such an optical system.

Conventional PDL measurement techniques use a test set that includes a laser, a manual polarization controller, and a power meter. The polarization controller is used to manually adjust the polarization of an optical signal from the laser through a wide range of polarization states. The power meter is then used to monitor the output of the device under test (DUT) for maximum and minimum signal transmission. PDL measurement error can be attributed to three primary sources: (1) the stability of the laser, (2) the fiber bend loss associated with adjustments of the manual polarization controller, and (3) PDL of the power meter (detector).

Commonly owned, copending U.S. patent application Ser. No. 07/999,080, filed Dec. 31, 1992, and titled "Depolarizer," discloses a means for decreasing the PDL of the power meter. A depolarizer (an unpumped erbium doped fiber) is interposed between the DUT and the power meter. The depolarizer converts the polarized light into unpolarized amplified spontaneous emission of a longer wavelength. The unpolarized amplified spontaneous emission reduces the effect of the PDL of the power meter.

While the system disclosed in the '080 application has led to an improvement in PDL measurement techniques, a flaw remains. Current PDL measurement techniques are empirical. For example, the polarization controller is used to incrementally adjust the optical signal through a range of polarizations in search of maximum and minimum signal transmission through the DUT. The searches are normally done manually, although automatic searches involving measurements at virtually all possible states of polarization (SOPs) have been proposed. Regardless of whether the search is manual or automatic, it is likely that the actual (absolute) maximum and minimum points will be missed, because the search is done in discreet increments.

Manual searches also have the disadvantage of operator fatigue which results from the tedious process required to manually adjust an optical signal through a range of polarizations. Operator fatigue leads to measurement errors.

More sophisticated techniques involving gradient search procedures also appear feasible. The major drawback to these methods is that they are potentially time consuming. For example, the points on the Poincare sphere can represent the sampled SOPs to be used as a test input. If a sample is made every 10° of longitude and latitude then roughly 600 measurements would form the sample set. This could take a considerable amount of time and is therefore not attractive as a manufacturing test procedure. In addition, for accurate PDL measurements one would have to be assured that the waveplates used to produce the sample SOP are without PDL.

SUMMARY OF THE INVENTION

Polarization dependent loss (PDL) of an optical component is computed in a deterministic way that requires only four measurements. Each measurement is taken using a different input state of polarization. Each polarization state is unique and at least one of the polarization states is elliptical.

The test set of the invention includes an optical source for generating an optical signal. A polarization controller produces a polarized input signal having one of four known polarization states. Connection means provides the polarized signal to the optical component or device under test (DUT). A power meter receives the polarized signal from the optical component under test and determines the intensity of the polarized signal out of the DUT.

A motor or similar actuator means cycles the polarization controller through the four known polarization states. A controller computes the PDL of the optical component based on the measured intensities of the polarized signals for the four known polarization states. The controller may also control the motor to change the polarization state of the input signal.

In the preferred embodiment, a depolarizer is positioned between the DUT and the power meter. The depolarizer is an unpumped doped optical fiber having a length sufficient to absorb fully the polarized signal and to produce unpolarized amplified spontaneous emission of longer wavelength from the polarized signal. By depolarizing the signal prior to measuring the intensity at the power meter, errors caused by the PDL of the power meter are substantially reduced (i.e., reduced to a level below current measurement capabilities).

In the preferred embodiment, the optical source includes a laser, a first optical isolator, an interference bandpass filter, and a second optical isolator. The polarization controller includes a first polarization controller coupled to receive the optical signal from the laser. The first polarization controller includes a fixed polarizer, a quarter waveplate, and a half waveplate. A second polarization controller is interposed between the laser and the first polarization controller. The second polarization controller is manually adjusted to maximize the optical signal being transmitted through the fixed polarizer of the first polarization controller.

The method of the invention includes the following steps. An optical signal is polarized to produce a signal having a first known polarization state. The first polarized signal is then transmitted through the DUT to yield a first output signal. The intensity $T_{O,a}$ of the first output signal is measured. These steps are then repeated for second, third and fourth polarization states to yield respective intensities $T_{O,b}$, $T_{O,c}$ and $T_{O,d}$. Each of the first, second, third and fourth polarization states are unique. At least one of the polarization states is elliptical (not linear).

The transmissivity of the optical component under test is represented by a Mueller matrix. The output intensity $T_O$ is a product of first row elements $m_{O1}$, $m_{O1}$, $m_{O2}$, and $m_{O3}$ of the Mueller matrix and a Stokes vector representing the polarized input signal. Thus, the intensities $T_{O,a}$, $T_{O,b}$, $T_{O,c}$ and $T_{O,d}$ can be used to compute values for the first row elements $m_{00}$, $m_{01}$, $m_{02}$, and $m_{03}$ of the Mueller matrix. Once these values are computed, the PDL of the optical component under test is computed using the following equation:

$$PDL = -10\log\left(\frac{m_{00} - a}{m_{00} + a}\right), \text{ where}$$

$$a = \sqrt{m_{01}^2 + m_{02}^2 + m_{03}^2}.$$

In the preferred embodiment, the test set is calibrated and a reference signal is used to normalize the intensity measurements to eliminate drift and other test measurement errors from the PDL computations. The reference signal is formed by tapping off a portion of each polarized signal at the connection means. The reference signal is used by the power meter to determine the change in input power at the DUT for each of the four polarization states. The intensity of the signal from the DUT and the intensity of the reference signal are measured by the power meter in the ratio mode. Prior to measuring the intensity of the optical signals, the signals may be depolarized to eliminate any PDL error introduced by the power meter.

The foregoing and other objects, features and advantages of the invention will be apparent from the following, more particular description of a preferred embodiment of the invention, as illustrated in the accompanying drawing.

BRIEF DESCRIPTION OF THE DRAWING

FIG. 1 is a block diagram illustrating the test set of the invention.

DETAILED DESCRIPTION OF THE PREFERRED EMBODIMENT

The inventors have discovered a deterministic method for measuring the polarization dependent loss (PDL) of an optical component. The method uses the Mueller matrix representation of a device under test (DUT). Four measurements are taken to characterize the PDL of the DUT. Each of the measurements is done with an input signal having a unique, known state of polarization (SOP). At least one of the inputs signals must have an elliptical (i.e., not linear) SOP. The intensities of the output signal from the DUT for each of these SOPs is then measured. The intensities are used to compute the first row elements $m_{00}$, $m_{01}$, $m_{02}$, and $m_{03}$ of the Mueller matrix. The first row elements are then used to compute the PDL of the optical component under test using the following equation:

$$PDL = -10\log\left(\frac{m_{00} - a}{m_{00} + a}\right),$$

where $$a = \sqrt{m_{01}^2 + m_{02}^2 + m_{03}^2}.$$

The preferred embodiment of the invention is discussed in detail below. While specific part numbers and configurations are discussed, it should be understood that this is done for illustration purposes only. A person skilled in the art will recognize that other components and configurations may be used without departing from the spirit and scope of the invention.

A test set 100 of the invention is shown in FIG. 1. Test set 100 includes an optical source 102, a polarization controller 104, an optical tap 106, a depolarizer 108, and a power meter (detector) 110. A DUT 112 is connected between optical tap 106 and depolarizer 108. All elements are connected via fusion spliced optical fibers. An electronic controller 118 is electrically connected to polarization controller 104 and power meter 110 to automate PDL measurements using test set 100.

With test input and output directly connected (i.e., with no DUT present), test set 100 has a residual PDL of less than 0.001 dB. If the temperature is kept constant, measurements with a repeatability of N0.01 dB are obtainable, yielding an order of magnitude improvement over conventional empirical PDL measuring techniques.

Optical Source 102

Optical source 102 includes a distributed feedback (DFB) laser 120, optical isolators 122,126, an interference bandpass filter 124 and a modulator 128. Laser 120, optical isolators 122,126 and bandpass filter 124 are connected via fusion spliced optical fibers. Modulator 128 is electrically connected to laser 120.

Laser 120 generates optical energy that lies within the absorption bandwidth of depolarizer 108 (discussed below). Modulator 128 modulates laser 120 at 10 MHz to reduce the coherence length of the laser. This arrangement provides laser 120 with a stability of less than 0.002 dB variation in a two minute interval. This variation, however, does not adversely affect the PDL measurement accuracy, because it is ratioed out through the use of reference channel 116 as discussed below.

Bandpass filter 124 has a 1.5 nm (nanometer) pass band. Bandpass filter 124 reduces the amplified spontaneous emission of laser 120. If laser 120 does not have output radiation of a wavelength outside of the depolarizer absorption bandwidth, then bandpass filter 124 and isolators 122,126 may be eliminated.

Polarization Controller 104

The output of isolator 126 is connected to polarization controller 104. Polarization controller 104 includes a manual polarization controller 130 and an automated polarization controller 132. Automated polarization controller 132 includes a polarizer, a quarter waveplate and a half waveplate, all mounted on a shaft for relative rotation by an electric motor. Manual polarization controller 130 is an all fiber polarization controller which is used to maximize the signal through the polarizer of automated polarization controller 132. Once the signal through the polarizer is maximized, the quarter and half waveplates may be rotated to change the SOP of the optical signal output from polarization controller 104.

In the preferred embodiment, manual polarization controller 130 is a three paddle, all fiber polarization controller such as a model MPC1000, available from BT&D Inc., Kennett Square, Pa. Automated polarization controller 132 is a model PR-2000, available from JDS Fitel Inc., Nepean, Ontario, Canada.

Polarization controller 104 is used to cycle the optical signal from optical source 102 through four states of polarization. This is accomplished by rotating the quarter and half waveplates in controller 132. In an alternate embodiment, special waveplates may be inserted and removed from the optical path to yield the desired states of polarization.

Optical Tap 106

Optical tap 106 is a single input, dual output optical splitter. The input of tap 106 is connected to the output of polarization controller 104. A first output 141 of tap 106 is connected to DUT 112. The intensity of this signal is measured by a first channel 114 of power meter 110.

A portion (e.g., one percent) of the optical signal input to tap 106 is tapped off to form a reference signal which is output via a second output 142. Second output 142 of tap 106 is connected to a second or reference channel 116 of power meter 110. The reference signal is used to determine the change in input power into DUT 112 for each of the four polarization states.

Depolarizer 108

Depolarizer 108 is a length of unpumped, erbium doped fiber which is used to convert the polarized light from DUT 112 to unpolarized amplified spontaneous emission of a longer wavelength. Depolarizer 108 operates as follows. When light in the erbium absorption band (i.e., 1460 nm to 1570 nm) is input to a length of unpumped erbium doped fiber, the light excites the erbium atoms. The excited atoms return to the ground state by emitting lower energy (longer wavelength) photons and, if the emitted photons are within the erbium absorption band, the process is repeated. Thus, amplified spontaneous emission is generated at successively longer wavelengths.

If the depolarizer fiber is sufficiently long, the input signal is completely absorbed and only longer wavelength, unpolarized amplified spontaneous emission is generated. For example polarized light at 1558 nm is converted to broadband unpolarized amplified spontaneous emission at wavelengths that are longer than 1600 nm. For a more detailed discussion of depolarizer 108, see the above referenced U.S. patent appl. Ser. No. 07/999,080, which is incorporated herein by reference. By providing a depolarized optical signal to power meter 110, errors caused by the PDL of power meter 110 are substantially reduced (i.e., reduced to a level below current measurement capabilities).

Power Meter 110

In the preferred embodiment, power meter 110 is an HP8153A power meter, available from Hewlett-Packard Company, Palo Alto, Calif.

Measurement are made in a ratio mode using the reference signal to account for slow drifts in test set 100.

Electronic Controller 118

Electronic controller 118 is electrically coupled to automated polarization controller 132 to control rotation of the quarter and half waveplates (via an electric motor) which are used to change SOPs of the optical signal. Controller 118 is also electrically connected to power meter 110 to coordinate SOP changes with intensity measurements taken by power meter 110. Electronic controller 118 includes processing means for computing a PDL for the DUT according to the method outlined below.

Electronic controller 118 may be any general purpose microcomputer or workstation having an appropriate interface for communicating with test set instruments. In the preferred embodiment, the computer will have an IEEE-488 interface for communication with the HP8153A power meter and the automated polarization controller.

Method of the Invention

Before using test set 100 to measure the PDL of a DUT, manual polarization controller 130 is adjusted for maximum transmission through the polarizer of automated polarization controller 132. This ensures that all of the input signal is aligned with the polarizer's axis to establish a reference for generation of the four desired SOPs. Automated polarization controller 132 is then set to generate each of the four desired SOPs.

Next, test set 100 is calibrated. Calibration involves determining the ratio between the input power to DUT 112 ($P_{out,cal}$) and the reference signal power ($P_{ref,cal}$) for each of the four polarization states. This is done by splicing the first output of optical tap 106 directly to depolarizer 108 (i.e., DUT 112 is bypassed). At each SOP, the intensity of the output of depolarizer 108 (via channel 114) and the reference signal (via channel 116) are measured via power meter 110 and stored in a memory by controller 118. This calibration information is used to determine changes in input intensities to the DUT.

After DUT 112 is spliced in, the transmitted power ($P_{out,DUT}$ through DUT 112) and reference power ($P_{ref,DUT}$) are measured at each desired polarization state. Thus, there are four measured quantities for each polarization state. The first two values are the output of the depolarizer ($P_{out,cal}$) and the reference channel ($P_{ref,cal}$) from the calibration measurement. The second two values are the same powers measured with the DUT present ($P_{out,DUT}$ and $P_{ref,DUT}$)

The change in transmitted power or the normalized power $T_O$ for each polarization state is given in decibels (dB) by:

$$T_O = (P_{out,DUT} - P_{out,cal}) - (P_{ref,DUT} - P_{ref,cal})$$

After all four measurements have been taken and To has been calculated for each SOP, then the changes in transmitted power are used to compute the first row elements $m_{00}$, $m_{01}$, $m_{02}$, and $m_{03}$ of the Mueller matrix. The first row elements are then used to compute the PDL of the DUT using the following equation:

$$PDL = -10\log\left(\frac{m_{00} - a}{m_{00} + a}\right),$$

where

-continued $$a = \sqrt{m_{01}^2 + m_{02}^2 + m_{03}^2}.$$

Note that the PDL is expressed in dB or decibels as is the convention. This, however, is not required.

Theoretical Foundation of the Invention

Transmission through a DUT for a given input may be expressed as the product of the Mueller matrix of the DUT and the Stokes vector describing the input. This is illustrated in Equation 1.1:

$$\begin{bmatrix} T_0 \\ T_1 \\ T_2 \\ T_3 \end{bmatrix} = \begin{bmatrix} m_{00} m_{01} m_{02} m_{03} \\ - - - - \\ - - - - \\ - - - - \end{bmatrix} * \begin{bmatrix} S_0 \\ S_0 \cos\omega \cos\alpha \\ S_0 \cos\omega \sin\alpha \\ S_0 \sin\omega \end{bmatrix} \quad (1.1)$$

$T_O$ is the intensity of the output signal (i.e., transmitted power). $S_O$ is the intensity of the input signal. $\omega$ is the ellipticity of the input polarization, and $\alpha$ is the azimuth of the input polarization. Except for the first row, all other entries in the Mueller matrix have been omitted to emphasize the fact that they do not enter into the PDL determination. We are concerned only with the $T_O$ term of the resultant Stokes vector.

Performing the indicated matrix multiplication results in Equation 1.2:

$$T_O = m_{00} S_O + m_{01} S_O \cos\omega \sin\alpha + m_{03} S_O \sin\omega \quad (1.2)$$

To obtain the maximum and the minimum values for the intensity variable $T_O$, the partial derivatives of Equation 1.2 are taken with respect to the input polarization variables $\omega$ and $\alpha$. The resulting equations are then set equal to zero.

For $\alpha$:

$$\delta T_O / \delta \alpha = -m_{01} S_O \cos\omega \sin\alpha + m_{02} S_O \cos\omega \cos\alpha = 0 \quad (1.3)$$

Simplification of Equation 1.3 yields:

$$m_{01} \sin\alpha = m_{02} \cos\alpha.$$

and therefore:

$$\alpha = \arctan(m_{02}/m_{01}) + n\pi, \; n = 0, 1 \quad (1.4)$$

$$\alpha = \alpha_0 + n\pi, \; n = 0, 1 \quad (1.4a)$$

The addition of $n\pi$ in Equation 1.4 comes from a consideration that the azimuth has a range of from zero to $2\pi$. The ellipticity, to be determined in what follows, has a range of $\pm\pi$. This is the range of the definition of the arctangent, and hence, there are no additional factors to be considered in its expression.

For $\omega$:

$$\delta T_O / \delta \omega = -m_{01} S_O \sin\omega \cos\alpha - m_{02} S_O \sin\omega \sin\alpha + m_{03} S_O \cos\omega \quad (1.5)$$
$$= 0$$

Solving for $\omega$ yields:

$$\omega = \arctan\left( \frac{m_{03}}{m_{01}\cos\alpha + m_{02}\sin\alpha} \right) \quad (1.6)$$

Applying Equation 1.4 to eliminate $\alpha$ yields:

$$\omega = \arctan\left( \frac{m_{03}}{\frac{m_{01}^2}{\sqrt{m_{01}^2 + m_{02}^2}} + \frac{m_{02}^2}{\sqrt{m_{01}^2 + m_{02}^2}}} \right)$$

This simplifies to:

$$\omega = \arctan\left( \frac{m_{03}}{\sqrt{m_{01}^2 + m_{02}^2}} \right)$$

Knowing the values of $\alpha$ and $\omega$ in terms of $m_{O1}$, $m_{O2}$, and $m_{O3}$ allows the following three relationships to be formed:

$$\cos\omega\cos\alpha = \left\{ \frac{\sqrt{m_{01}^2 + m_{02}^2}}{\sqrt{m_{01}^2 + m_{02}^2 + m_{03}^2}} \right\} * \left\{ \frac{m_{01}}{\sqrt{m_{01}^2 + m_{02}^2}} \right\} = \quad (1.71)$$

$$\frac{m_{01}}{\sqrt{m_{01}^2 + m_{02}^2 + m_{03}^2}}$$

$$\cos\omega\sin\alpha = \frac{m_{02}}{\sqrt{m_{01}^2 + m_{02}^2 + m_{03}^2}} \quad (1.72)$$

and $$\sin\omega = \frac{m_{03}}{\sqrt{m_{01}^2 + m_{02}^2 + m_{03}^2}} \quad (1.73)$$

For use below, we define:

$$a = \sqrt{m_{01}^2 + m_{02}^2 + m_{03}^2} \quad (1.74)$$

Equations 1.71–1.73, representing the azimuth and ellipticity of the polarization, can then be used in conjunction with Equation 1.74 to rewrite Equation 1.1 as follows:

$$\begin{bmatrix} T_0 \\ T_1 \\ T_2 \\ T_3 \end{bmatrix} = \begin{bmatrix} m_{00} m_{01} m_{02} m_{03} \\ - - - - \\ - - - - \\ - - - - \end{bmatrix} * \begin{bmatrix} S_0 \\ S_0 m_{01}/a \\ S_0 m_{02}/a \\ S_0 m_{03}/a \end{bmatrix} \quad (1.8)$$

Performing the indicated multiplication (with n=0 in Equation 1.4) leads to an expression in Equation 1.9 for the maximum output intensity:

$$T_{Omax} = S_O(m_{00} + m^2_{O1}/a + m^2_{O2}/a + m^2_{O3}/a) \quad (1.9)$$

Equation 1.9can be simplified to:

$$T_{Omax} = S_O(m_{00}+a) \quad (1.10)$$

Next, the minimum output intensity is computed. When n=1 in Equation 1.4a, the following relationships are true:

$$\cos(\alpha_O + \pi) = -\cos \alpha_O$$

$$\sin(\alpha_O + \pi) = \sin \alpha_O$$

These relationships are used to rewrite Equation 1.6 as:

$$\omega = \arctan\left( \frac{m_{03}}{-(m_{01}\cos\alpha_O + m_{02}\sin\alpha_O)} \right)$$

Simplifying yields:

$$\omega = -\arctan\left( \frac{m_{03}}{m_{01}\cos\alpha_O + m_{02}\sin\alpha_O} \right)$$

Thus, the Stokes vector for the minimum is simply:

$$\begin{bmatrix} S_0 \\ -S_0 m_{01}/a \\ -S_0 m_{02}/a \\ -S_0 m_{03}/a \end{bmatrix}$$

As can be seen, this vector is 180° away from the maximum case (see Equation 1.8) on the Poincare sphere. Thus, the polarizations for maximum and minimum are in quadrature. Associating this vector with the assumed Mueller matrix leads to the result:

$$T_{Omin} = S_O(m_{00} - a) \quad (1.11)$$

The PDL can now be calculated from Equations 1.10 and 1.11 as follows:

$$PDL = -10\log(T_{Omin}/T_{Omax}) = -10\log\left( \frac{m_{00} - a}{m_{00} + a} \right) \quad (1.12)$$

EXAMPLE

From Equation 1.12, it is apparent that the measurement of $m_{00}$, $m_{P1}$, $m_{O2}$, and $m_{O3}$ is required to determine the PDL of the DUT. This can be done with four equations, each one involving a unique input SOP. The simultaneous solution of the four resulting Stokes vectors will isolate the desired Mueller matrix elements. For example, the following four unique input SOPs may be used to determine the first row elements of the Mueller matrix:

1. A horizontal linear polarized source
2. A vertical linear polarized source
3. A 45° linear polarized source
4. A circular polarized source The accuracy and precision are those associated with the intensity measurements. Using separate polarizations also has the attendant advantage of utilizing a priori knowledge conveniently.

For the sample SOPs given above, the Mueller matrix element could be computed as follows. For an input signal of horizontal linearly polarized light (S=$S_O$, $S_O$, O,O), the transmitted intensity ($T_O$) is given by:

$$T_{Oa} = S_O m_{00} + S_O m_{01}$$

where $S_O$ is the input power. Similarly, for vertical linearly polarized light (S=$S_O - S_O$, O,O) of the same power:

$$T_{O,b} = S_O m_{00} - S_O m_{01}$$

These two equations can then be solved for $m_{00}$ and $m_{01}$ in terms of the input and transmitted powers.

A similar approach is used for $m_{O2}$ and $m_{O3}$ using 45° linear polarized light and left hand circular polarized light. For an input signal of 45° linear polarized light (S=$S_O$0,$S_O$,0 ), the transmitted intensity ($I_t$) is given by:

$$T_{O,c} = S_O m_{O2} + S_O m_{00}$$

Similarly, for left hand circular polarized light (S=$S_O$,O,O,$-S_O$) of the same power:

$$T_{O,d} = S_O m_{00} - S_O m_{O3}$$

Because $m_{00}$ has been previously computed, these two equations can be solved for $m_{O2}$ and $m_{O3}$ in terms of the input ($S_O$) and transmitted ($T_O$) powers.

Thus, there will be four $T_O$ values, ($T_{O,a}, T_{O,b}, T_{O,c}$ and $T_{O,d}$), one for each polarization. The Mueller matrix elements are then given by:

$$m_{00} = \frac{T_{0,a} + T_{0,b}}{2}$$

$$m_{01} = \frac{T_{0,a} - T_{0,b}}{2}$$

$$m_{02} = T_{0,c} - \frac{T_{0,a} + T_{0,b}}{2}$$

$$m_{03} = \frac{T_{0,a} + T_{0,b}}{2} - T_{0,d}$$

Note that all values have been normalized for an input power of 1 mW (one milliWatt) and all values are in mW's to simplify the equations. Once the four Mueller matrix elements have been calculated, the PDL of the DUT may be computed from Equation 1.12.

In summary, the PDL of a DUT may be computed by taking an intensity measurement for each of four distinct SOPs. At least one of the SOPs must be elliptical (not linear) in order to solve for the Mueller matrix element $m_{O3}$. Once the Mueller matrix elements are computed, calculation of the PDL may be quickly performed.

While the invention has been particularly shown and described with reference to several preferred embodiments thereof, it will be understood by those skilled in the art that various changes in form and details may be made therein without departing from the spirit and scope of the invention as defined in the appended claims.

We claim:

1. A method for computing polarization dependent loss of an optical component, the method comprising the steps of:

(a) generating an optical input signal;

(b) polarizing said input signal to produce a polarized signal having a first known polarization state;

(c) transmitting said polarized signal through said optical component to yield an output signal, wherein a transmissivity of the optical component is represented by a Mueller matrix, an intensity $T_{O,a}$ of said output signal being a product of first row elements $m_{O0}$, $m_{O1}$, $m_{O2}$, and $m_{O3}$ of said Mueller matrix and a Stokes vector representing said polarized signal;

(d) measuring said intensity $T_{O,a}$ of said output signal;

(e) repeating steps (b)–(d) for second, third and fourth polarization states to yield respective intensities $T_{O,b}$, $T_{O,c}$ and $T_{O,d}$, wherein each of said first, second, third and fourth polarization states are unique and one of said polarization states is not linear;

(f) computing values for said first row elements $m_{O0}$, $m_{O1}$, $m_{O2}$, and $m_{O3}$ of said Mueller matrix using said intensities $T_{O,a}$, $T_{O,b}$, $T_{O,c}$ and $T_{O,d}$, and (g) computing the polarization dependent loss (PDL) of the optical component from said first row elements $m_{O0}$, $m_{O1}$, $m_{O2}$, and $m_{O3}$ of said Mueller matrix.

2. The method of claim 1, wherein step (g) of computing comprises using an equation:

$$PDL = -10\log\left(\frac{m_{00} - a}{m_{00} + a}\right),$$

where $$a = \sqrt{m_{01}^2 + m_{02}^2 + m_{03}^2}.$$

3. The method of claim 2, further comprising a step of:

normalizing each said intensity $T_O$ prior to step (f) to eliminate test measurement errors from the computations of step (g).

4. The method of claim 3, wherein said step (d) of measuring comprises:

depolarizing said output signal to produce a depolarized output signal; and measuring an intensity of said depolarized output signal with a power meter.

5. The method of claim 4, wherein said step of depolarizing comprises passing said output signal through an unpumped doped optical fiber to produce from said output signal unpolarized amplified spontaneous emission of longer wavelength; and wherein said step of measuring comprises measuring said intensity of said spontaneous emission with a power meter.

6. A method for computing polarization dependent loss of an optical component using a test set, the method comprising the steps of:

(a) generating an optical input signal;

(b) polarizing said optical input signal to produce a polarized signal having a first known polarization state;

(c) tapping off a portion of said polarized signal to produce a test signal and a reference signal;

(d) measuring an intensity of each of said test signal and said reference signal for said first known polarization state with a power meter;

(e) repeating steps (b)–(d) for second, third and fourth polarization states, wherein each of said first, second, third and fourth polarization states are unique and one of said polarization states is not linear;

(f) introducing the optical component into the test set so that said test signal is passed through the optical component prior to step (d);

(g) repeating steps (a)–(e);

(h) using, for said first polarization state, said intensity of said reference signal and said test signal measured prior to step (f), and said reference signal measured after step (f), to normalize said intensity of said test signal measured after step (f), said normalized intensity $T_{O,a}$ representing an intensity loss at said first polarization state resulting from said optical component;

(i) repeating step (h) for second, third and fourth polarization states to yield respective normalized intensities $T_{O,b}$, $T_{O,c}$ and $T_{O,d}$, (j) computing values for first row elements $m_{O0}$, $m_{O1}$, $m_{O2}$, and $m_{O3}$ of a Mueller matrix from said normalized intensities $T_{O,a}$, $T_{O,b}$, $T_{O,c}$ and $T_{O,d}$, and (k) computing the polarization dependent loss (PDL) of the optical component from said first row elements $m_{O0}$, $m_{O1}$, $m_{O2}$, and $m_{O3}$ of said Mueller matrix.

7. The method of claim 6, wherein step (k) of computing comprises using an equation:

$$PDL = -10\log\left(\frac{m_{00} - a}{m_{00} + a}\right),$$

where $$a = \sqrt{m_{01}^2 + m_{02}^2 + m_{03}^2}.$$

8. An apparatus for measuring polarization dependent loss of an optical component, comprising:

laser means for generating an optical signal;

polarization means for receiving said optical signal and for producing a polarized signal having one of four known polarization states, wherein each of said polarization states is unique and one of said polarization states is not linear;

connection means for providing said polarized signal to the optical component;

meter means for receiving said polarized signal from the optical component and for determining an intensity of said polarized signal;

actuation means, coupled to said polarization means, for causing said polarization means to cycle through said four known polarization states; and controller means, coupled to said meter means, for computing the polarization dependent loss of said optical component based on said measured intensities of said polarized signals for said four known polarization states.

9. The apparatus of claim 8, wherein said meter means comprises:

a depolarizer configured to depolarize said polarized signal to produce a depolarized signal; and a power meter coupled to said depolarizer to measure an intensity of said depolarized signal.

10. The apparatus of claim 9, wherein said depolarizer comprises an unpumped doped optical fiber having a length sufficient to produce from said polarized signal unpolarized amplified spontaneous emission of longer wavelength, said spontaneous emission forming said unpolarized signal.

11. The apparatus of claim 9, wherein said connection means comprises:
an optical splitter to tap off a portion of each polarized signal to produce a reference signal, each reference signal being provided to said power meter.

12. The apparatus of claim 9, wherein said laser means comprises:
a distributed feedback laser;
a first optical isolator coupled to receive said optical signal from said laser;
an interference bandpass filter coupled to receive said optical signal from said first optical isolator; and
a second optical isolator coupled to receive said optical signal from said interference bandpass filter.

13. The apparatus of claim 12, wherein said polarization means comprises:
a first polarization controller coupled to receive said optical signal from said laser means, said polarization controller having a fixed polarizer, a quarter waveplate, and a half waveplate; and
a second polarization controller interposed between said laser means and said first polarization controller and configured to be manually adjustable to maximize an optical signal being transmitted through said fixed polarizer of said first polarization controller.

14. The apparatus of claim 13, wherein said actuation means comprises:
an electric motor configured to change orientation of said waveplates of said first polarization controller to cycle said polarization means through said four known polarization states.

15. The apparatus of claim 14, wherein said electric motor is controlled by said controller means.

* * * * *